(12) United States Patent
Miller et al.

(10) Patent No.: US 6,403,623 B1
(45) Date of Patent: Jun. 11, 2002

(54) HETEROCYCLIC ANTITUBERCULOSIS AGENTS

(75) Inventors: Marvin J. Miller, South Bend; Jingdan Hu, Carmel, both of IN (US)

(73) Assignee: Unuversity of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 09/578,834

(22) Filed: May 25, 2000

Related U.S. Application Data

(60) Provisional application No. 60/136,249, filed on May 27, 1999.

(51) Int. Cl.[7] ...................... A61K 31/425; A61K 31/42; A61K 31/415
(52) U.S. Cl. ...................... 514/365; 514/374; 514/385; 514/924
(58) Field of Search ................................. 514/365, 374, 514/385, 924

(56) References Cited

U.S. PATENT DOCUMENTS 5,952,492 A * 9/1999 Geraci et al. ................ 540/524

OTHER PUBLICATIONS

Total Synthesis of a Mycobactin, Maurer, P., Miller, M., J. Am. Chem. Soc., 1983, 105, 240.
Total Synthesis of a Mycobactin S, . . . Hu, J., Miller M., J. Am. Chem. Soc., 1997, 119, 3462–3468.
Total Synthesis of Mycobactin Analogues, Xu, Y., Miller, M., J. Org. Chem., 1998, 63, 4314–4322.
Iron Chelators from mycobacteria . . . Vergne, A.F., et al., Nat. Prod. Rep., 2000, 17, 99–116.

* cited by examiner

Primary Examiner—Kevin E. Weddington
(74) Attorney, Agent, or Firm—William B. Scanlon

(57) ABSTRACT

Method for treating tuberculosis with 2-(2-substituted-phenyl)-2-oxazolines and related 5-membered heterocycles represented by the formula

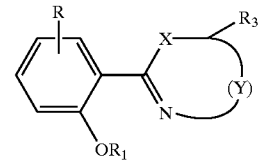

wherein Y is

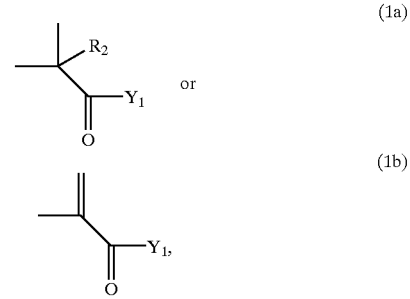

$Y_1$ is e.g. an ester or amide forming group, and X is O, S, or NH; and pharmaceutically acceptable formulations useful therein are provided. A preferred method comprises administering (S)-benzyl2-[2-(benzyloxy)phenyl]-2-oxazoline-4-carboxylate in a suitable formulation.

The compounds of the above formula are prepared by known methods, e.g. the oxazolines are obtained by coupling a substituted benzoic acid with a serine ester or threonine ester and cyclizing the coupled product.

16 Claims, No Drawings

HETEROCYCLIC ANTITUBERCULOSIS AGENTS

CROSS-REFERENCE TO RELATED APPLICATION

This application is a non-provisional application claiming the benefit of Provisional application serial No. 60/136,249 filed May 27, 1999.

STATEMENT REGARDING FEDERALLY SPONSORED RESEARCH

The invention described and claimed herein was sponsored by the National Institutes of Health Grant No. R01 GM25845.

BACKGROUND OF THE INVENTION

Field of Invention

This invention relates to the treatment of infectious diseases, certain heterocyclic compounds useful as therapeutic agents therein and, to pharmaceutical formulations containing said therapeutic agents. In particular this invention relates to a method for treating *Mycobacterium tuberculosis* infections in man, certain carboxy substituted 2-aryloxazoline, 2-arylthiazoline, 2-arylimidazoline compounds and similarly substituted related unsaturated heterocyclic compounds e.g. oxazole, thiazole and imidazole compounds, and to pharmaceutical formulations comprising said heterocyclic compounds.

Among bacterial infections, tuberculosis is usually a respiratory infection, although it can cause damage to virtually any organ in the human body. It is estimated that about 40% of the world's population is infected with the tuberculosis bacterium. Early in this decade, the incidence of tuberculosis began rising after a 33-year downward trend. Streptomycin, the first antibiotic capable of killing the tuberculosis organism, was discovered in 1944. Other antituberculosis agents were subsequently developed. (Lemke, T. L. In *Principles of Medicinal Chemistry*, 4th ed.; Foye, W. O., Lemke, T. L. Williams & Wilkins: Baltimore, 1995; pp 747–758.) However, the recent emergence of drug resistant strains of tuberculosis has raised serious concern. Between 1989 and 1992 drug resistant strains had appeared in 17 states. (Tuberculosis and HIV Public Health Policy: A Dual Challenge. Washington: AIDS Action Foundation, March 1992). Recently, studies on the application of siderophore substituted mycobactins and analogs thereof were reported (Xu, Yanping, and Miller, Marvin J. *J. Org. Chem.*, 1998,63, 4314). It was found that structural variations of the natural mycobactins produced by the mycobacterium were effective inhibitors of the mycobacterium. The retrograde synthesis work on the mycobactins carried out in this study has led to the discovery of the antituberculosis therapeutic agents of this invention.

SUMMARY OF THE INVENTION

The compounds provided by this invention are useful in the method described herein for the treatment of tuberculosis and are represented by the following formula 1.

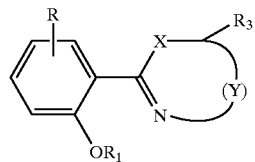

Formula 1 wherein X is O, S, or NH,

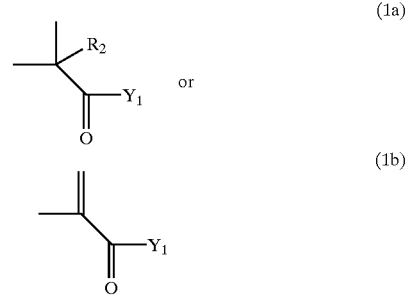

Y represents fragments $Y_1$ is $OR_4$, wherein $R_4$ is hydrogen, $C_1$–$C_4$ alkyl, phenyl, benzyl, diphenylmethyl, or a biologically-labile ester, —$NHR_4'$, or —$NHNHR_4'$ wherein $R_4'$ is hydrogen, $C_1$–$C_4$ alkyl, phenyl, benzyl, diphenylmethyl, or a 5- or 6-membered saturated or unsaturated heterocycle containing from 1 to 3 of the same or different nitrogen, oxygen or sulfur hetero atoms, and wherein said phenyl, benzyl, diphenylmethyl and $R_4'$ groups can be substituted by R as defined herein;

R is hydrogen or a substituent group e.g. lower alkyl, halogen, alkoxy, amino, substituted amino, hydroxy, carboxy or aminocarbonyl;

$R_1$ is hydrogen, alkyl, 5- to 7- membered cycloalkyl, alkyl substituted by phenyl or diphenyl, e.g. benzyl or diphenylmethyl, or a t-vinyl or ethinyl group represented by the formulas —$C(C_1$–$C_3)_2$—CH=$CH_2$, —$C(C_1$–$C_3)_2$—C≡CH;

$R_2$ is hydrogen or $C_1$–$C_3$ alkyl; and $R_3$ is hydrogen or lower alkyl;

The compounds represented by the formula 1 inhibit the growth of *Mycobacterium tuberculosis* and are useful in the treatment of tuberculosis in man when administered in an effective non toxic amount. Pharmaceutical formulations comprising a compound of the formula 1 or a pharmaceutically acceptable salt thereof and a suitable carrier are useful in the method for treating tuberculosis.

DETAILED DESCRIPTION

The terms used in the above formula 1 have the following meanings herein

R is hydrogen, $C_1$–$C_4$ alkyl such as methyl, ethyl, n-propyl, iso-propyl, n-butyl, iso-butyl, sec-butyl, or t-butyl; $C_1$–$C_4$ alkoxy such as methoxy, ethoxy, n-propoxy, iso-propoxy, n-butoxy, t-butoxy and the like; $C_1$–$C_4$ alkoxy substituted by phenyl, diphenyl such as benzyloxy diphenylmethoxy, 2-phenylethoxy, 1,2-diphenylethoxy, 3-phenylpropoxy, 2,2-diphenylethoxy, and the like; halogen such as fluoro, chloro, or bromo; hydroxy; carboxy; cyano; aminocarbonyl; amino, mono- or di-$C_1$–$C_4$ alkyl)aminocarbonyl such as dimethylaminocarbonyl, methylaminocarbonyl, ethylaminocarbonyl, diethylaminocarbonyl, iso-propylaminocarbonyl, n-propylaminocarbonyl, t-butylaminocarbonyl, and the like; amino and mono- or di-$C_1$–$C_4$ alkyl)amino such as methylamino, ethylamino, t-butylamino, dimethylamino, diethylamino, methylethylamino, n-propylamino, and the like;

$R_1$ is hydrogen, $C_1$–$C_4$ alkyl as exemplified for the term R above; 5- to 7-membered cycloalkyl such as cyclopentyl, cyclohexyl, cycloheptyl and the like; a di-$C_1$–$C_3$ alkyl) carbinyl ethinyl or vinyl-t-carbinyl group of the formula —C($C_1$–$C_3$)$_2$CH=CH$_2$ or —C($C_1$-$C_3$)$_2$—CH=CH$_2$ such as dimethylethinylcarbinyl, dimethylvinylcarbinyl, methylethylethinylcarbinyl, diethylethinylcarbinyl and the like; $C_1$–$C_4$ alkyl substituted by phenyl or diphenyl such as benzyl, diphenylmethyl, 2-phenylethyl, 2,2-diphenylethyl, 1,3-diphenylpropyl and, wherein said phenyl and diphenyl groups can be substituted by a group R as defined herein above;

$R_2$ is hydrogen or $C_1$–$C_3$ alkyl;

$R_3$ is hydrogen or $C_1$–$C_4$ alkyl;

$R_4$ is hydrogen, $C_1$–$C_4$ alkyl, phenyl, benzyl, diphenylmethyl or a biologically-labile ester;

$R_4{}'$ hydrogen, $C_1$–$C_4$ alkyl, phenyl, benzyl, diphenylmethyl, or a 5- or 6-membered saturated or unsaturated heterocyclic ring containing from 1 to 3 of the same or different nitrogen, oxygen, or sulfur hetero atoms such as for example, pyridyl, piperidyl, pyrrolidyl, pyrrolidinyl, pyrimidyl, pyrazolyl, furyl, thienyl, thiazolyl, oxazolyl, thiazinyl or tetrazolyl, and wherein said phenyl, benzyl, diphenylmethyl and heterocyclic ring groups can be substituted by R substituents having the same meanings as defined herein above.

When $R_4$ is a biologically-labile ester, $R_4$ represents an acyloxymethyl group, —CH$_2$—C(O)-alk, a acyloxyalkyl group, alk-C(O)O—CH-alk or alk-OC(O)O—CH-alk, a alkoxyethyl ether group, alk-O-(CH$_2$)$_2$—O—CH$_2$—, where in the foregoing alk is $C_1$–$C_4$ alkyl, or is $R_4$ phthalidyl, indanyl, or a 2-oxo-1,3-dioxolene group represented by the formula.

Examples of such labile ester groups are acetoxymethyl, propionoxymethyl, pivaloyloxymethyl, 2-(methoxy)ethoxymethyl, 2-(ethoxy)ethoxymethyl, and 2-(t-butoxy)ethoxymethyl, and like labile ester moieties.

The compounds represented by the formula 1 having basic or acidic groups form salts with mineral acids and organic acids and inorganic and organic bases respectively. For example, when an R substituent is a basic group such as an amino or substituted amino group or when $R_4$ is a basic heterocyclic group such as piperidyl or pyridyl, salts can be formed with mineral acids such as hydrochloric, hydrobromic, sulfuric and phosphoric acids. Organic acids which can be used are e.g. the sulfonic acids such as methanesulfonic, benzenesulfonic, toluenesulfonic, or naphthalenesulfonic; benzoic, chlorobenzoic, salicylic, malonic, maleic and succinic acids. Acidic groups e.g., when R is a carboxy group, form salts with basis such as sodium hydroxide, potassium hydroxide, calcium hydroxide, sodium carbonate, sodium or potassium bicarbonate and ammonia. Also such acidic groups form salts with organic bases such as alkylamines e.g., methylamine, t-butylamine, diethylamine, cyclohexylamine, dicyclohexylamine, abietylamine, diethanolamine, and ethanolamine. Such salts are useful in the isolation and purification of formula 1 compounds and in the preparation of pharmaceutical formulations for administration in the therapeutic method provided herein.

Preferred compounds of the invention are represented by the formula 1 wherein Y is the fragment (1a) or (1b) and X is O or S. In particular, of the preferred compounds are those wherein $R_1$ is benzyl or diphenylmethyl and $Y_1$ is OR$_4$ wherein $R_4$ is benzyl or diphenylmethyl are preferred. Among this preferred group, the compound (S)-Benzyl 2-[2-(benzyloxy)phenyl]-2-oxazoline-4-carboxylate, in in vitro tests inhibited 98% of the growth of *M. tuberculosis* H37R at a concentration of 12.5 µg/mL.

According to the method provided by this invention *Mycobacterium tuberculosis* infections in man are treated by administering to the infected host an effective, non toxic amount, of a compound represented by the formula 1 or a pharmaceutically acceptable non toxic salt thereof. An effective amount of the compound of formula 1, in general, is between about 2 mg/kg of host body weight and about 25 mg/kg. The compound of formula 1 or a pharmaceutically acceptable salt thereof may be administered in a single daily dose or in multiple doses throughout the day. The amount administered and the particular dose regimen employed by the physician may vary depending on such factors as the severity of the disease, the duration of the infection prior to treatment, the age and general health of the infected host and the tolerance of the particular host to the treatment. The compound represented by the formula 1 or a pharmaceutically acceptable salt thereof may be administered parenterally or orally in a suitable pharmaceutical formulation. The route of administration may be determined by the acceptance of the dose regime by the individual host. Parenteral administration is achieved via im. injection or via iv. For such administration the compound or a salt thereof is formulated in a suitable diluent such as physiological saline, glucose or dextrose solution or Ringer's solution and the like. For iv. administration the drip method can be employed as well as the piggy back method wherein the drug formulation is added slowly to the host along with other fluids such as mineral solutions or nutrients such as glucose and amino acids. For oral administration a compound of the invention or a salt thereof can be formulated into gelatin capsules, e.g. in 250 mg and 500 mg doses, in tablet form or as a liquid solution or suspension.

The invention also provides pharmaceutical formulations for use in the above-described method. The formulations comprise a compound of the formula 1 or a pharmaceutically acceptable non toxic salt thereof and a pharmaceutically acceptable carrier. Suitable carriers for im. or iv. administration include for example, deionized sterile water, physiological saline, 5% glucose and like commonly use carriers. Tablets may be formulated with the drug and binding agents, solubilizing agents, fillers and the like. Liquid suspensions which may be used can comprise the drug and water, a flavoring agent, solubilizing agent, coloring agent, a preservative and the like.

The pharmaceutical formulations provided herein may be made up in unit dosage form. For example, a formulation comprising 100 mg of the compound or a salt thereof and a pharmaceutically acceptable carrier. Other unit dosage formulations comprise 1 g of the drug or salt form thereof and a pharmaceutically acceptable carrier or 500 mg of the compound of formula 1 or a salt thereof and a pharmaceutically acceptable carrier. For im. administration the unit dose may be incorporated in sterile ampoules or vials while for iv. administration the unit dose may be provided in sterile bottles adaptable to hook up with tubing for the drip method with controls for regulating the rate of flow.

The compounds of the invention represented by the formula 1 are prepared by synthetic routes which depend upon the heterocyclic ring desired where, in formula 1, X is O, S, or NH. The compounds where, in the formula 1, Y is the fragment (1a) and X is O (oxazolines) are prepared by coupling an ester of the amino acid ester, HO—CH($R_3$)—CH(NH$_2$)—C(O)ester, e.g. an ester of serine or threonine, with a 2-($R_1$O)benzoic acid to provide the amide, N-[2-($R_1$O)benzoyl]-NHCH—[CH($R_3$)—OH]—C(O)ester The coupling reaction can be carried out via formation of an active ester of the acid such as that formed with 1-hydroxy-7-azabenzotriazole or via treatment of the acid and amine with a carbodiimide. The amide is then cyclized with Burgess' reagent (methoxycarbonylsulfamoyltriethylammonium hydroxide inner salt) to yield the ester of 2-[2-($R_1$O)phenyl]-2-oxazoline-4-carboxylic acid. The preparation is illustrated with serine and threonine in the following reaction scheme 1.

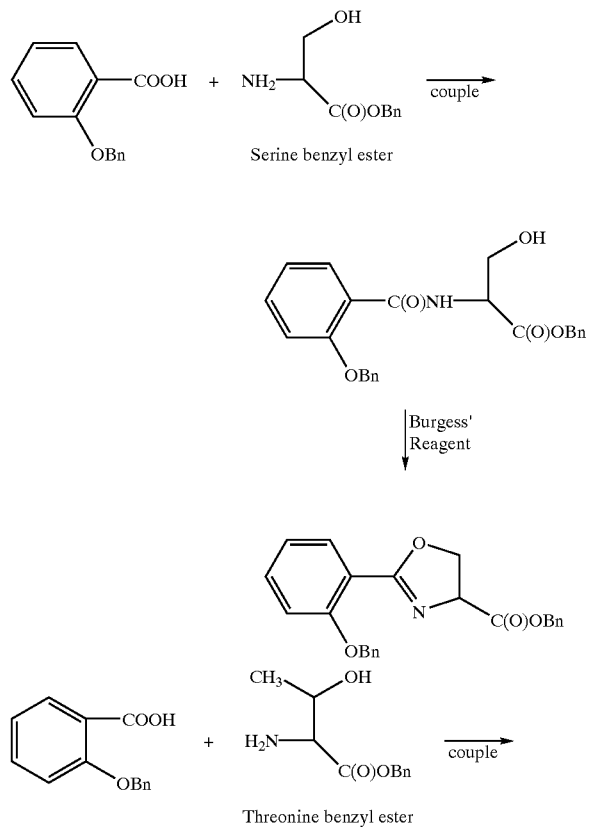

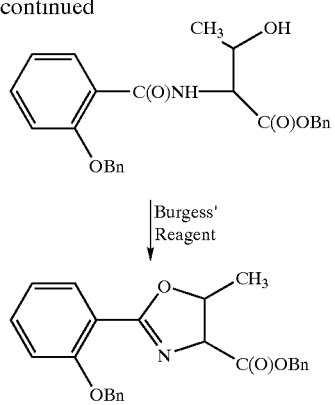

In Reaction Scheme 1 Bn represents benzyl.

The thiazoline compounds represented by the formula 1, X is S, wherein Y is the fragment (1a) are prepared in a similar manner. The amino acid ester is coupled with the acid to form the amide, N-[2-($R_1$O)benzoyl]-NH—CH—[CH($R_3$)—OH]—C(O)ester, and the amide is cyclized with Lawesson's reagent (2,4-bis(p-methoxyphenyl)-1,3-dithiadiphosphetane-2,4-disulfide as shown with serine and threonine in the following Reaction Scheme 2.

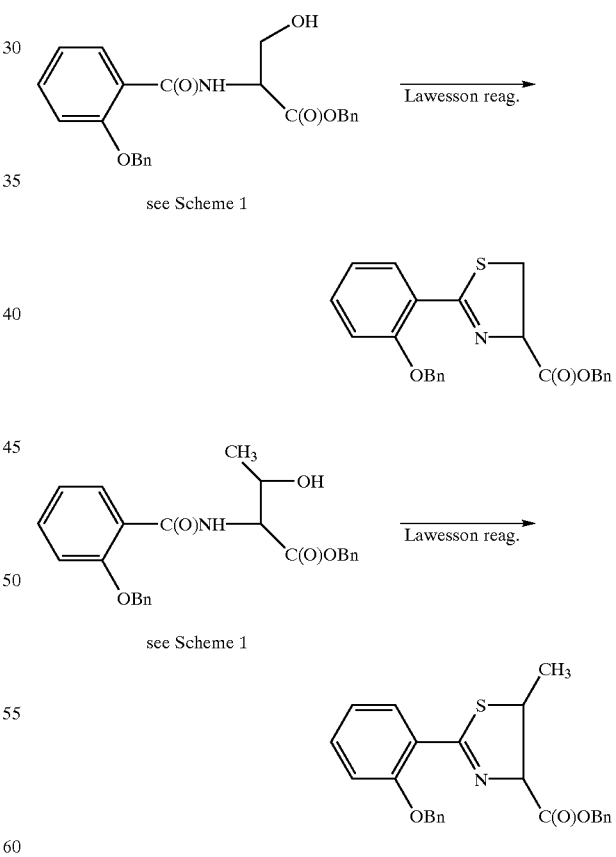

The imidazolidine compounds represented by the formula 1 where X is NH and Y is the fragment (1a) are prepared by coupling a 2-$R_1$O substituted benzoic acid with a 2,3-diaminopropionic acid ester wherein the 3-amino group is protected to form the amide, N-[2-($R_1$O)benzoyl]—NH—CH—[CH($R_3$)—NH$_2$]—C(O)ester, wherein the free amino group is protected. The coupling is carried out with an active ester of the carboxylic acid or with a carbodiimide. Following the coupling reaction the amino protecting group of the amide formed is removed to form the amino substituted amide, and the amino amide is cyclized to form the imidazolidine ring via dehydrative cyclization as depicted below.

Reaction Scheme 3

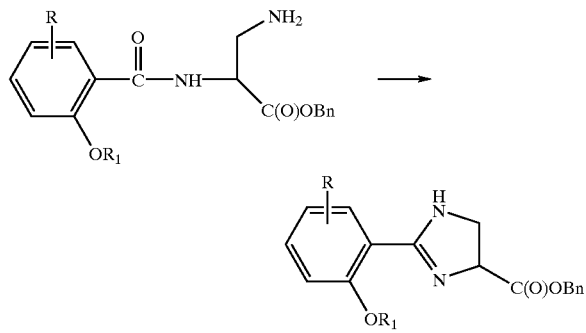

The 2,3-diaminopropionic acid esters, NH$_2$—CH—[CH(R$_3$)—NH$_2$]—C(O)ester, are prepared as follows. t-Boc protected serine, HOCH$_2$CH(NH-t-Boc)COOH, is coupled with O-benzylhydroxylamine at pH 4–5 with EDC HCl to provide the hydroxamate, HOCH$_2$CH(NH-t-Boc)CONHOBn. The latter is cyclized in acetonitrile with triphenylphosphene-carbon tetrachloride in the presence of triethylamine to form the β-lactam, 1-benzyloxy-3-t-Boc-aminoazetidin-2-one. The β-lactam is then saponified with lithium hydroxide to provide, in 100% yield, the 2,3-diaminopropionic acid derivative, BnONHCH$_2$CH(NH-t-Boc)COOH. In the above Bn is benzyl. The carboxylic acid group of the derivative obtained is esterified for use in the coupling reaction of Reaction scheme 3. The OBn protecting group is left intact during the coupling reaction while the t-Boc protecting group is removed to provide the free amino group involved in the coupling. Following amide formation the OBn group is removed via hydrogenation to provide the free amino amide ester for cyclization to the imidazoline. The above sequence of reactions is illustrated below.

HOCH$_2$CH(NHBOC)COOH + BnONH$_2$ ⟶

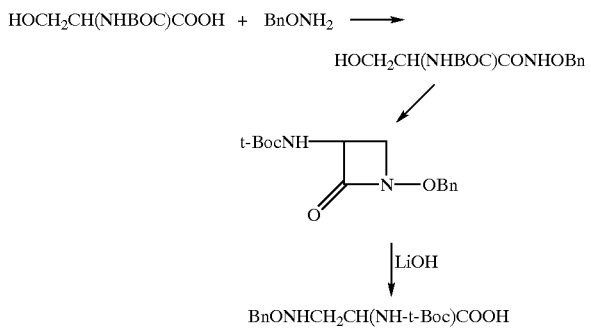

Compounds represented by the formula 1 where Y is the fragment (1a) and R$_2$ is C$_1$–C$_3$ alkyl are obtained with the corresponding oxazoline, thiazoline or imidazoline compound e.g., a methyl or benzyl 2-[2-(benzyloxy)phenyl]-2-oxazoline-5-H, or 5-(C$_1$–C$_4$ alkyl)-4-carboxylate, by reaction at about −78° C. in an inert solvent such as THF with a C$_1$–C$_3$ alkyl iodide in the presence of a base such as sodium dimethylsilylamide as depicted in the following.

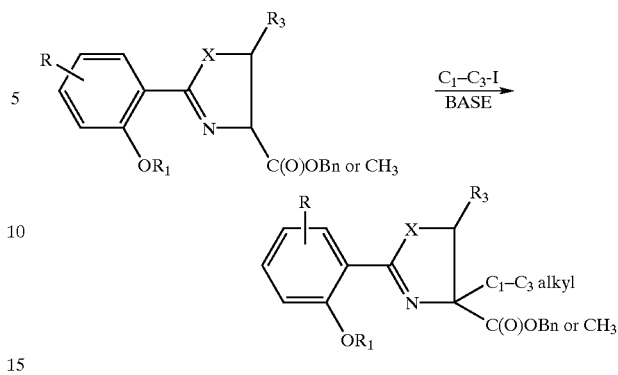

The oxazole, thiazole and imidzole compounds represented by the formula 1 wherein Y is the fragment (1b) are obtained by dehydrogenation of the corresponding oxazoline, thiazoline or imidazoline by treatment with a dehydrogenation reagent such as DDQ. The reaction is carried out at a temperature of about 50° C. and about 75° C. in an inert solvent such as benzene and is illustrated below.

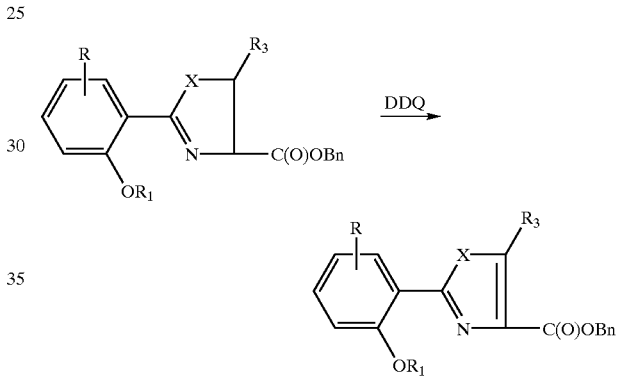

The compounds represented by the formula 1 wherein Y$_1$ is —NH—R$_4$' are prepared by the reaction of an ester of (1a) or (1b), Y$_1$=C(O)OR$_4$, wherein OR$_4$ is e.g. C$_1$–C$_4$ alkoxy or an acyl halide of the carboxy group, (Y$_1$=C(O)OH, R$_4$=H), with the NH$_2$R$_4$' amine. The compounds wherein Y$_1$ is —NHNHR$_4$' can be obtained by the reaction of the hydrazine H$_2$NNHR$_4$' with the acyl halide or ester of the carboxy group. Compounds of the formula 1 wherein R$_4$' is a heterocycle e.g. pyridine, are prepared by reacting the acyl halide or the ester of Y$_1$ with an amino substituted pyridine, e.g. 4-aminopyridine. The compounds wherein Y$_1$ is —NHNHR$_4$' are obtained by reacting the heterocyclic hydrazine with the acid halide or the ester wherein, OR$_4$ is e.g. an alkoxy group, to provide the corresponding amide or hydrazide. Examples of heterocyclic substituted compounds are represented by the following formulas wherein Het represents the heterocyclic ring.

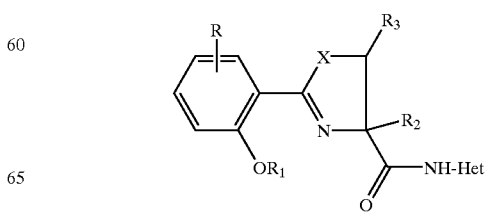

-continued

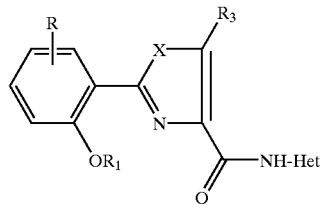

Het can be 2- or 4-pyridyl, 2- or 4-piperidyl, 3-thienyl, 2-(1,3-thiazolyl), 3-pyrimidyl, 2-oxazolyl, 1H-tetrazolyl and like heterocycles. The hydrazino compounds where in the above formulas —NH—Het is replaced by —NHNH—Het like heterocycles are represented by Het.

In carrying out the preparation of the compounds represented by the formula 1 as shown above, when any of the groups represented by R, $R_1$ or $R_4$ bear an amino or carboxylic acid substituent, these groups are best protected with a commonly used protecting group to prevent untoward side reactions caused by participation of the unprotected amino or carboxy groups. Amino protecting groups which may be used for temporary protection of an amino group include, among many, tert-butyloxycarbonyl, benzyloxycarbonyl, p-nitrobenzylcarbonyl, trichloroacetyl, silyl groups such as trimethylsilyl, t-butyldiethylsilyl, t-butyldiphenylsilyl and the like, enamines such as those formed with ethyl acetoacetate or methyl acetoacetate, and like amino protecting groups. The carboxylic acid substituent can be protected with such groups as a silyl group such as those listed above, benzyl, p-nitrobenzyl, t-butyl, and the like. The particular group chosen will be one that is removed under conditions differing from the conditions employed in the desired reaction so that the protecting group will survive the desired reaction and thereafter be removed to obtain the product.

The following examples are provided to further illustrate the methods for preparing the compounds of the invention and are not to be considered as limitations of the invention.

In the examples the following abbreviation designations of reagents have the indicated meanings:

FABMS—fast atom bombardment mass spec.

HREIMS—high resolution electron impact mass spec.

DCC—dicyclohexylcarbodiimide

EDC—ethyldimethylaminopropylcarbodiimide

DDQ—dichlorodicyanoquinone

HOAt—1-hydroxy-7-azabenzoaminotriazole

THF—tetrahydrofuran

1*, 2* or 3* refers to once, twice or three times Burgess's reagent—(methoxycarbonylsulfamoyl) triethylammonium hydroxide inner salt [Wipf, P.; Miller, C. P. *J. Org. Chem.* 1993, 58, 1575] Lawesson's reagent—2,4-bis(p-methoxyphenyl)-1,3-dithiaphosphetane=2,4-disulfide

PREPARATIONS

The following are the preparations of compounds used to make the compounds of the invention in the examples which follow the preparations.

Preparation 1

2-(Benzyloxy)benzoic Acid

To a solution of salicylic acid (7 g, 0.05 mol) in methanol (100 mL) at −78° C., $SOCl_2$ (8 mL, 0.11 mol, 2.2 equiv.) was added dropwise. The reaction mixture was stirred at 40° C. overnight, concentrated and extracted with EtOAc. The organic layer was washed with $NaHCO_3$, brine, dried over $Na_2SO_4$, filtered and concentrated. The product was then dissolved in DMF; BnBr (9 mL, 0.075 mol, 1.5 equiv.), $K_2CO_3$ (27.5 g, 0.2 mol, 4 equiv.) and NaI (75 mg) were added. The reaction mixture was stirred at room temperature for 12 h, diluted with EtOAc, washed with water, 0.5N HCl, and brine, dried over $Na_2SO_4$, filtered, concentrated and chromatographed on silica gel eluting with hexanes/EtOAc (10:1), to give methyl 2-(benzyloxy)benzoate as an oil (6.8 g, 0.03 mol, 57%). To the methyl ester was added KOH (3.2 g, 0.06 mol, 2 equiv.) and $THF/H_2O$ (1:1) (20 mL). The reaction mixture was stirred at room temperature overnight and extracted with EtOAc. The aqueous layer was acidified to pH 2 with 2N HCl and extracted with EtOAc. The combined organic layers were washed with brine, dried over $Na_2SO_4$, filtered and concentrated to afford 2-(benzyloxy)benzoic acid as white crystals (m=4.5 g, 70%).

Preparation 2

N-[2-(Benzyloxy)benzoyl]-L-Serine Benzyl Ester

Carbodiimide Method

To a stirred solution of 2-(benzyloxy)benzoic acid 3.53 g, 15.5 mmol) and L-serine benzyl ester hydrochloride (3.27 g, 14 mmol) in $CH_2Cl_2$ (70 mL) was added $Et_3N$ (2.09 mL, 15 mmol) and 1-ethyl-3-(3-dimethylaminopropyl)carbodiimide (2.96 g, 15.5 mmol). After being stirred for 10 h at room temperature under argon, the reaction mixture was diluted with $CH_2Cl_2$ (200 mL), washed with $H_2O$, saturated $NaHCO_3$ solution, 5% citric acid aqueous solution, $H_2O$, brine, dried over $Na_2SO_4$, filtered, and concentrated. Recrystallization from toluene afforded the title compound (5.12 g, 90%), as white crystals: $R_f$=0.41 (EtOAc/$CH_2Cl_2$= 1/5); mp 116–118°; $[\alpha]^{23}D$=+24.1° (c=1.0, $CH_2Cl_2$); IR (KBr) 3500–3100, 1740, 1620 cm$^{-1}$; $^1$H NMR (300 MHz, $CDCl_3$) δ8.81 (d, J=6.9 Hz, 1H, NH), 8.19 (dd, J 1=7.8 Hz, J 2=1.8 Hz, 1H, ArH), 7.46–7.25 (m, 11H, ArH), 7.10–7.04 (m, 2H, ArH), 5.21–5.11 M, apparently 4 overlapping doublets, 4H, 2{$CH_2$ phenyl}), 4.90–4.85 (m, 1H, CH), 3.93–3.89 (m,2H, $CH_2OH$), 2.32 (br, 1H, OH); $^{13}$C NMR (75 MHz, $CDCl_3$) δ170.13, 165.56, 156.91, 135.50, 135.26, 133.17, 132.31, 128.74, 128.53, 128.33, 128.06, 127.99, 121.48, 121.09, 112.79, 71,23, 67,17, 63.61, 55.38; FABMS: 406 (M+1). Anal. calcd. for $C_{23}H_{21}NO_5$: C, 70.58; H, 5.41; N, 3.58, found: C, 70.43; H, 5.60; N, 3.37.

Active Ester-Carbodiimide Method

To a stirred solution of 2-(benzyloxy)benzoic acid (2.0 g, 8.7 mmol), L-serine benzyl ester hydrochloride (2.0 g, 8.7 mmol, 1 equiv.) and HOAt (1.2 g, 8.7 mmol, 1 equiv.) in DMF (200 mL) was added triethylamine (0.98 mL, 9.6 mmol, 1.1 equiv.) and EDC HCl (2.02 g, 4.8 mmol, 1.2 equiv.). After being stirred overnight at room temperature under nitrogen, the reaction mixture was diluted with ethyl acetate (200 mL), washed with 1N HCl (60 mL), saturated $NaHCO_3$, saturated $NH_4Cl$ (60 mL), and brine (60 mL). The combined organic layers were dried over $Na_2SO_4$, filtered, concentrated and chromatographed on silica gel eluting with $CH_2Cl_2$/MeOH (95/5) to give the title compound, N-[2-(benzyloxy)benzoyl]-L-serine benzyl ester, 92.5 g, 70%) as white crystals. $R_f$=0.5 ($CH_2Cl_2$/MeOH, 95/5); $^1$H NMR (300 MHz, $CDCl_3$) δ8.80 (d, 1H, NH), 8.19 (dd,1H, ArH), 7.46–7.24 (m, 11H, ArH), 7.12–7.04 (m, 2H, ArH), 5.21–5.11 (m, 4H, 2{$CH_2$phenyl}), 4.91–4.87 (m, 1H, CH), 3.93–3.90 (m, 2H, $CH_2OH$), 2.2 (1H, OH).

EXAMPLE 1

(S)-Benzyl 2-[2-(Benzyloxy)phenyl]-2-oxazoline-4-carboxylate (1)

To a stirred solution of N-[2-(benzyloxy)benzoyl]-L-serine benzyl ester (545 mg, 1.35 mmol) in THF (10 mL)

was added Burgess' reagent, (methoxycarbonylsulfamoyltriethylammonium hydroxide, inner salt), 360 mg, 1.55 mmol, 1.1 equiv.). After being refluxed for 30 min at room temperature under argon, the reaction mixture was diluted with EtOAc (100 mL), washed with $H_2O$, brine, dried over $Na_2SO_4$, filtered, concentrated and chromatographed on silica gel eluting with EtOAc/$CH_2Cl_2$ (1/15) to yield oxazoline 1 (343 mg, 66%), as a white, amorphous solid: $R_f$=0.58 (EtOAc/$CH_2Cl_2$=1/15); mp 69–71° C. (recrystallized from EtOAc and hexanes); IR (KBr) 1732, 1630 cm−1; 1H NMR (300 MHz, $CDCl_3$) δ7.81 (dd, 1H, J 1=7.8 Hz, J 2=1.8 Hz, ArH), 7.50–7.47 (m, 2H, ArH), 7.42–7.26 (m, 9H, ArH), 7.00–6.96 (m, 2H, ArH), 5.28 (d, J=12.3 Hz, 1H, PhHH), 5.20 (d, J=11.7 Hz, 1H, PhHH), 5.18 (s, 2H, $CH_2Ph$), 5.00 (dd, J 1=10.5 Hz, J 2=8.1 Hz, 1H, $CHCH_2$), 4.68–4.52 (m, 2H, $CHCH_2$); $^{13}C$ NMR (75 MHz, $CDCl_3$) δ171.03, 165.65, 157.56, 136.79, 135.40, 132.64, 131.62, 128.50, 128.36, 128.29, 128.25, 127.53, 126.69, 120.67, 117.12, 113.75, 70.55, 69.16, 68.77, 67.12; FABMS: 388 (M+1); HREIMS calcd. for $C_{24}H_{21}NO_4$ 387.1471, found 387.1458.

EXAMPLE 2

(S)-2-[2-(Oxy)phenyl]-2-oxazoline-4-carboxylic Acid (2)

(S)-Benzyl 2-[2-(benzyloxy)phenyl]-2-oxazoline-4-carboxylate (1) (250 mg) was dissolved in methanol (20 mL). After purging with nitrogen gas for 30 min, the catalyst palladium on carbon (10%) (25 mg) was added. After being purged with $H_2$ gas for 30 min, the reaction mixture was stirred for 1 h under 1 atm $H_2$. The catalyst was then filtered on celite and the solvent was evaporated to afford the desired product in quantitative yield.

EXAMPLE 3

(S)-2-[2-(Benzyloxy)phenyl]-2-oxazoline-4-carboxylic acid (3)

To a mixture of benzyl ester (1) (25.7 mg, 0.0664 mmol) in 1:1 THF/$H_2O$ (3 mL) at 0° C. was added LiOH (9 mg, 0.348 mmol, 1.5 equiv.). The reaction mixture was stirred for 1 h at room temperature. The desired product 3 was obtained in 99% yield after purification by column chromatography ($CH_2Cl_2$/MeOH=85:15). FABMS: 298 (M+1); HREIMS calcd. for $C_{17}H_{15}NO_4$ 298.1079, found 298.1078.

EXAMPLE 4

(S)-Methyl 2-[2-(Benzyloxy)phenyl]-2-oxazoline-4-carboxylate (4)

Compound (3) was esterified with methyl alcohol to provide (4).

EXAMPLE 5

(S)-Methyl 2-[2-(Oxy)phenyl]-2-oxazoline-4-carboxylate (5)

Oxazoline (4) (25 mg) was dissolved in methanol (3 mL). After purging with nitrogen gas for 30 min, the catalyst palladium on carbon (10%) (2.5 mg) was added. After being purged with $H_2$ gas for 30 min, the reaction mixture was stirred for 1.5 h under 1 atm $H_2$. The catalyst was then filtered through a pad of celite and the solvent was evaporated to afford the desired product 5 in 95% yield.

EXAMPLE 6

(S)-isopropyl 2-[2-(Benzyloxy)phenyl]-2-oxazoline-4-carboxylate (6)

2-(Benzyloxy) benzoic acid (190.93 g, 0.048 mol) and L-serine isopropyl ester hydrochloride (8.8 g, 0.048 mol) were placed in $CH_2Cl_2$ (250 mL) and cooled on ice. $Et_3N$ (6.66 mL, 0.048 mol) was added, followed by DCC (12.38 g, 0.06 mol). The solution was stirred at 0° C. for 1 h and then at room temperature for 3 h. The mixture was concentrated to 140 mL, chilled and filtered. The filtrate was washed twice with 5% $Na_2CO_3$ and once with 0.5 N HCl. Excess DCC was destroyed by stirring with HOAc (0.5 mL) and $H_2O$ (10 mL) for 20 min and then filtering. The solvent was dried ($MgSO_4$), chilled and refiltered. Evaporation of solvent left 14.5 g (85%) of L-N-(2-(benzyloxy)benzoyl) serine isopropyl ester as an oil. Some of this oil (9.15 g, 25.6 mmol) was dissolved in ether (150 mL) and chilled on ice. $SOCl_2$ (5.5 mL) was added such that the temperature remained below 5° C. After stirring at 0° C. for 100 min, more $SOCl_2$ (3 mL) was added. Two more portions of $SOCl_2$ (each 3 mL) were added in 100 min intervals. Then the reaction mixture was left at −20° C. overnight. The resulting crystals were collected by centrifugation at 4° C. and washed by suspending in ice-cold ether and recentrifuging. The supernatant was returned to the freezer. The crystals were distributed between 10% $Na_2CO_3$ and ether. The ether layer was washed with 10% $Na_2CO_3$, dried ($MgSO_4$), filtered, and evaporated to leave 4.812 g of needles. A further 1.006 g of the oxazoline (6) was obtained from the supernatant after 24 more hours at −20° C., with the same workup as above. Total yield: 5.818 g (67%); mp (ether/hexanes) 61–62° C.; $^1H$ NMR (300 MHz, $CDCl_3$) δ7.7–8.0 (m, 1H), 7.2–7.7 (m, 6H), 6.8–7.2 (m, 2H), 5.2 (s, 2H), 5.0 (m, 1H), 4.6 (m, 3H), 1.3 (d, 6H).

EXAMPLE 7

(S)-Benzy 2-[2-(Benzyloxy)phenyl]-2-thiazoline-4-carboxylate (7)

N-[2-(Benzyloxy)benzoyl]-L-serine benzyl ester (20 mg, 0.05 mmol) and Lawesson's reagent (2,4-bis(p-methoxyphenyl)-1,3-dithiadiphosphetane-2,4-disulfide) (20 mg, 0.05 mmol, 1 equiv.) were dissolved in toluene (15 mL). After being refluxed overnight under nitrogen, the reaction mixture was diluted with EtOAc (20 mL), washed with brine, dried over $MgSO_4$, filtered, concentrated and chromatographed on silica gel eluting with hexanes/EtOAc (6/1) to yield thiazoline (7) as a clear oil. $R_f$=0.3 (hexanes/EtOAc=6:1); $^1H$ NMR (300 MHz, $CDCl_3$) δ8.00 (dd,1H, ArH), 7.51–7.49 (m, 2H, ArH), 7.42–7.25 (m, 9H, ArH), 7.02–6.95 (m, 2H, ArH), 5.28 (d, 1H, PhCHH), 5.20 (d, 1H, PhCHH), 5.18 (s, 2H, $CH_2Ph$), 5.12 (dd, 1H, $CHCH_2$), 3.60–3.47 (m, 2H, $CHCH_2$); MS (FAB) m/z 404 MH$^+$, measured exact mass: 404.1313, calculated exact mass: 404.1320.

EXAMPLE 8

Benzyl 2-[2-(Benzyloxy)phenyl]-2-oxazoline-4-methyl-4-carboxylate (8)

Oxazoline (1) (1 g, 2.6 mmol) dissolved in freshly distilled THF (30 mL) was cooled to −78° C. After addition of methyl iodide (1.83 g, 800 μL, 13 mmol, 5 equiv.) and stirring at −78° C. for 10 min, sodium dimethylsilyl amide (1M in THF) (4 mmol, 4 mL, 1.5 equiv) was added slowly via a syringe. After stirring at −78° C. for 45 min, a few drops of water were added to the reaction mixture which was then allowed to warm up to room temperature. The THF was evaporated and the residue was taken-up in EtOAc/$H_2O$. The aqueous layer was re-extracted with EtOAc and the combined organic layers were washed with brine, dried over sodium sulfate, filtered and concentrated. Purification of the crude by column chromatography (hexanes/EtOAc=4/1) afforded the racemic desired product (8) as a colorless oil (0.810 g, 78%). $R_f$=0.58 (hexanes/EtOAc=4/1); $^1$H NMR (300 MHz, CDCl$_3$) δ7.70–5.95 (m, 16H, ArH), 5.30–5.20 (q, 2H, CH$_2$Ph), 5.20 (s, 2H, CH$_2$Ph), 4.85 (d, 1H, CHH), 4.20 (d, 1H, CHH), 1.65(s, 3H, CH$_3$).

EXAMPLE 9

(S) 2-[2-(Benzyloxy)phenyl]-2-oxazoline-4-methyl-4- Carboxylic Acid (9)

To a solution of oxazoline (8) (180 mg, 0.45 mmol) dissolved in THF/water (1:1) (6 mL) was added potassium hydroxide (51 mg, 0.9 mmol, 2 equiv.). After being stirred overnight at room temperature, the reaction mixture was extracted with EtOAc. The aqueous layer was acidified with 1N HCl and re-extracted with EtOAc. The combined organic layers were washed with brine, dried over sodium sulfate, filtered and concentrated to afford the desired product in 65% yield (91.4 mg) as a clear oil. $^1$H NMR (300 MHz, CDCl$_3$) δ7.65 (d, 1H, ArH), 7.40 (m, 1H, ArH), 7.05 (d, 1H, ArH), 6.90 (t, 1H, ArH), 4.85 (d, 1H, CHH), 4.20 (d, 1H, CHH), 1.65 (s, 3H, CH$_3$).

EXAMPLE 10

(S) 2-[2-(Oxy)phenyl]-2-oxazoline-4-methyl-4-carboxylic Acid (10)

Oxazoline (8) (30 mg, 0.075 mmol) was dissolved in methanol (4 mL). After purging with nitrogen gas for 30 min, the catalyst palladium on carbon (10%) (4 mg) was added. After being purged with H$_2$ gas for 30 min, the reaction mixture was stirred for 1.5 h under 1 atm H$_2$. The catalyst was then filtered off on celite and the solvent evaporated to afford the desired product (10) in 94% yield. %). $R_f$=0.20 (methanol/EtOAc=1/9).

EXAMPLE 11

(S)-Benzyl 2-[2-(Benzyloxy)phenyl]-2-oxazoline-5-methyl-4-carboxylate (11)

To a stirred solution of N-[2-(benzyloxy)benzoyl]-L-threonine benzyl ester (409 mg, 0.976 mmol) in THF (20 mL) was added Burgess' reagent (methoxycarbonylsulfamoyltriethylammonium hydroxide, inner salt,) 350 mg, 1.46 mmol, 1.5 equiv.). After being stirred at room temperature under nitrogen overnight and refluxed for 1 h, the reaction mixture was diluted with EtOAc, washed with NH$_4$Cl , brine, dried over Na$_2$SO$_4$, filtered, concentrated, and chromatographed on silica gel eluting with EtOAc/CH$_2$Cl$_2$ (1/15) to yield oxazoline (11) (76%). $^{13}$C NMR (600 MHz, CDCl$_3$) δ169.768, 165.810, 157,604, 136.811, 135.341, 132.532, 131.625, 128.566, 128.566, 128.486, 128.350, 128.278, 127.550, 126.874, 120.668, 117,574, 113.677, 77.398, 71.552, 70.617, 66.768, 16.047; FABMS: 402 (M+1); calculated exact mass (M+1): 402.1705, measured exact mass (M+1): 402.1717.

EXAMPLE 12

(S)-Methyl 2-[2-(Benzyloxy)phenyl]-2-oxazoline-5-methyl-4-carboxylate (12)

To a stirred solution of N-[2-(benzyloxy)phenyl]-L-threonine methyl ester (31 mg, 0.09 mmol) in THF (2 mL) was added Burgess' reagent, (methoxycarbonylsulfamoyltriethylammonium hydroxide, inner salt, 32.3 mg, 0.14 mmol, 1.5 equiv.). After being stirred at room temperature under nitrogen overnight and refluxed for 1 h, the reaction mixture was diluted with EtOAc, washed with NH$_4$Cl, brine, dried over Na$_2$SO$_4$, filtered, concentrated, and chromatographed on silica gel eluting with EtOAc/CH$_2$Cl$_2$ (1/15) to yield oxazoline (12) (80.5%). $^{13}$C NMR (600 MHz, CDCl$_3$) δ170.432, 165.713, 157.601, 136.804, 132.551, 131.590, 128.269, 127.579, 126.899, 120.656, 117.542, 113.570, 77.737, 71.692, 70.581, 51.953, 16.108; FABMS: 326 (M+1); calculated exact mass (M+1): 326.1392, measured exact mass (M+1): 326.1383.

EXAMPLE 13

(S) 2-[2-(Oxy)phenyl]-2-oxazoline-5-methyl-4-carboxylic Acid (13)

Oxazoline (11) (50 mg) was dissolved in methanol (5 mL). After purging with nitrogen gas for 30 min, the catalyst palladium on carbon (10%) (5 mg) was added. After being purged with H$_2$ gas for 30 min, the reaction mixture was stirred for 1.5 h under 1 atm H$_2$. The catalyst was then filtered off on celite and the solvent evaporated to afford the desired product (13) in 99% yield. $^{13}$C NMR (600 MHz, CDCl$_3$) δ171.611, 167.442, 159.871, 134.152, 128.152, 128.412, 118.743, 116.752, 109.809, 77.628, 69.690, 49.276, 15.913; FABMS: 222 (M+1); calculated exact mass (M+1): 222.0766, measured exact mass (M+1): 222.0768.

EXAMPLE 14

(S)-Benzyl 2-[2-(Benzyloxy)phenyl]-2-thiazoline-5-methyl-4-carboxylate (14)

N-[2-(Benzyloxy)benzoyl]-L-threonine benzyl ester (50 mg, 0.119 mmol) and Lawesson's reagent (2,4-bis(p-methoxyphenyl)-1,3-dithiadiphosphetane-2,4-disulfide) (24 mg, 0.06 mmol, 0.5 equiv.) were dissolved in toluene (2.5 mL). After being refluxed under nitrogen, the reaction mixture was diluted with EtOAc, washed with brine, dried over MgSO$_4$, filtered, concentrated and chromatographed on silica gel eluting with hexane/EtOAc (6/1) to yield thiazoline (14) in 40% yield. $^1$H NMR (300 MHz, CDCl$_3$) δ7.95 (dd,1H, ArH), 7.51–7.49 (d, 2H, ArH), 7.45–7.25 (m, 9H, ArH), 7.05–6.95 (m, 2H, ArH), 5.24 (s, 2H, CH$_2$Ph), 5.19 (s, 2H, CH$_2$Ph), 4.82 (d, 1H, CH), 4.20 (p, 1H, CH), 1.25 (d, 3H, CH$_3$); FABMS: 418 (M+1); calculated exact mass (M+1): 418.1477, measured exact mass (M+1): 418.1472.

EXAMPLE 15

Benzyl 2-[2-(Benzyloxy)phenyl]-2-oxazole-4-carboxylate (15)

Oxazoline (1) (40.7 mg, 0.105 mmol) and DDQ (26.3 mg, 0.116 mmol, 1.1 equiv.) were dissolved in benzene (3 mL). The reaction mixture mixture was refluxed for 2 h, cooled at room temperature and then diluted with CH$_2$Cl$_2$. It was washed with 2N NaOH, NH$_4$Cl , brine, dried over Na$_2$SO$_4$, filtered, concentrated and chromatographed on silica gel eluting with CH$_2$Cl$_2$/MeOH (95/5) to yield oxazole 15 in 80.5% yield. $R_f$=0.33 (CH$_2$Cl$_2$/MeOH=95/5). 1H NMR (300 MHz, CDCl$_3$) δ8.30 (s,1H, CH), 8.05 (dd, 1H, ArH), 7.55–7.25 (m, 11H, ArH), 7.10–7.05 (t, 2H, ArH), 5.40 (s, 2H, PhCH$_2$), 5.20 (s, 2H, PhCH$_2$).

EXAMPLE 16

Methyl 2-[2-(Benzyloxy)phenyl]-2-oxazole-5-methyl-4-carboxylate (16)

Oxazoline (12) (717 mg, 2.21 mmol) and DDQ (551 mg, 2.43 mmol, 1.1 equiv.) were dissolved in benzene (35 mL).

The reaction mixture was refluxed for 2 h, cooled at room temperature and then diluted with EtOAc (100 mL). It was washed with 2N NaOH (2*20 mL), 0.5 HCl (1*20 mL), brine 3*20 mL), dried over $Na_2SO_4$, filtered, concentrated and chromatographed on silica gel eluting with hexanes/EtOAc (3/1) to yield oxazole (16) as a white solid in 86% yield. mp=78.5–79.5° C. $R_f$=0.1 (hexanes/EtOAc=3/1). 1H NMR (300 MHz, $CDCl_3$) δ8.02 (dd, 1H, ArH), 7.56 (d, 2H, ArH), 7.42–7.26 (m, 4H, ArH), 7.06–7.00 (m, 2H, ArH), 5.20 (s, 2H, $CH_2Ph$), 3.95 (s, 3H, $CO_2CH_3$), 2.65 (s, 3H, $CH_3$); $^{13}C$ NMR (600 MHz, $CDCl_3$) δ162.931, 158.468, 156.603, 156.069, 136.657, 131.953, 130.617, 128.271, 127.997, 127.610, 126.694, 120.874, 116.304, 113.330, 70.358, 51.755, 11.937. HEIMS: 323 (M); calculated exact mass: 323.1158, measured exact mass: 323.1176.

EXAMPLE 17

2-[-(Benzyloxy)phenyl]-2-oxazole-5-methyl-4-carboxylic Acid (17)

To a mixture of methyl ester (16) (75 mg, 0.232 mmol) in 1:1 $THF/H_2O$ (5 mL) at 0° C. was added LiOH (9 mg, 0.348 mmol, 1.5 equiv.). The reaction mixture was stirred for 30 min at 0° C. and then was allowed to warm-up to room temperature. The desired oxazole (17) was obtained in 98% yield as a white solid. $^1H$ NMR (300 MHz, $CDCl_3$) δ10.17 (s, 1H, OH), 8.04 (dd, 1H, ArH), 7.60–7.54 (d, 2H, ArH), 7.46–7.26 (m, 4H, ArH), 7.10–7.02 (m, 2H, ArH), 5.21 (s, 2H, $CH_2Ph$), 2.70 (s, 3H, $CH_3$); $^{13}C$ NMR (300 MHz, $CDCl_3$) δ166.399, 158.595, 157.118, 156.697, 136.611, 132.221, 130.624, 128.398, 127.724, 127.657, 126.781, 121.001, 116.030, 113.437, 70.478, 12.15; FABMS: 310 (M+1); calculated exact mass (M+1): 310.1079, measured exact mass (M+1): 310.1063.

EXAMPLE 18

2-[2-(Oxy)phenyl]-2-oxazole-5-methyl -4-carboxylic Acid (18)

Oxazole (17) (0.838 mmol) was dissolved in methanol (15 mL). After purging with nitrogen gas for 30 min, the catalyst palladium on carbon (10%) (45 mg) was added. After being purged with $H_2$ gas for 30 min, the reaction mixture was stirred for 6 h under 1 atm $H_2$. The catalyst was then filtered off through a pad of celite and the solvent evaporated to afford the desired product (18). $^1H$ NMR (300 MHz, $CDCl_3$) δ7.60 (d, 1H, ArH), 7.20–7.10 (td, 1H, ArH), 6.80 (d, 1H, ArH), 6.73 (t, 1H, ArH), 4.45 (1H, OH), 2.50 (s, 3H, $CH_3$); $^{13}C$ NMR (600 MHz, $CDCl_3$); $^{13}C$ NMR (300 MHz, $CDCl_3$) δ163.185, 158.762, 156.470, 154.899, 132.241, 126.915, 125.665, 119.170, 116.691, 109.936, 11.349.

We claim:

1. A method for treating *Mycobacterium tuberculosis* infections in man which comprises administering to said man a therapeutically effective non-toxic dose of a compound of the formula

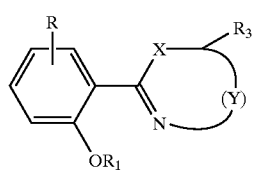

wherein Y is the fragment

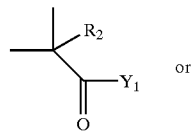 (1a)

or

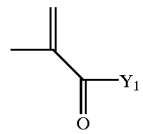 (1b)

wherein

Y is the fragment (1a)

$Y_1$ is $OR_4$, $NHR_4'$ or $NHNHR_4'$;

X is O, S, or NH,

R is hydrogen, $C_1$–$C_4$ alkyl; $C_1$–$C_4$ alkoxy, $C_1$–$C_4$ alkoxy substituted by phenyl or diphenyl; halogen, hydroxy, carboxy, cyano, aminocarbonyl, di-($C_1$–$C_4$ alkyl) aminocarbonyl, amino, or mono- or di-($C_1$–$C_4$ alkyl) amino;

$R_1$ is hydrogen, $C_1$–$C_4$ alkyl, 5- to 7-membered cycloalkyl, a di-($C_1$–$C_3$ alkyl) vinyl group of the formula —C($C_1$–$C_3$ alkyl)$_2$CH=$CH_2$, a di-($C_1$–$C_3$ alkyl) t-carbinyl group of the formula —C($C_1$–$C_3$ alkyl)$_2$—C≡CH, $C_1$–$C_4$ alkyl and $C_1$–$C_4$ alkyl substituted by phenyl or diphenyl wherein said phenyl and diphenyl groups can be substituted by a group R as defined hereinabove;

$R_2$ and $R_3$ are independently hydrogen or $C_1$–$C_4$ alkyl;

$R_4$ is hydrogen, $C_1$–$C_4$ alkyl, phenyl, benzyl, diphenylmethyl, or a biologically-labile ester;

$R_4'$ is hydrogen, $C_1$–$C_4$ alkyl, phenyl, benzyl, diphenylmethyl, or a 5- or 6-membered saturated or unsaturated heterocyclic ring containing 1 to 3 nitrogen, oxygen or sulfur ring hetero atoms, and wherein said phenyl, benzyl, diphenylmethyl and heterocyclic ring groups can be substituted by a group R as defined hereinabove; and the pharmaceutically acceptable non-toxic salts thereof.

2. The method of claim 1 wherein X is O or S and Y is the fragment (1a).

3. The method of claim 2 wherein X is O.

4. The method of claim 3 wherein $R_2$ and $R_3$ independently are hydrogen or $C_1$–$C_4$ and $Y_1$ is $OR_4$.

5. The method of claim 4 wherein $R_2$ is hydrogen and $R_4$ is hydrogen or diphenylmethyl.

6. The method of claim 5 wherein (S)-benzyl 2-[2-(benzyloxy)phenyl]-2-oxazoline-4-carboxylate is administered.

7. The method of claim 5 wherein benzyl 2-[2-(benzyloxy)phenyl]-2-oxazoline-4-methyl-4-carboxylate is administered.

8. The method of claim 5 wherein benzyl 2-[2-(benzyloxy)phenyl]-2-oxazoline-5-methyl-4-carboxylate is administered.

9. The method of claim 2 wherein X is S.

10. The method of claim 9 wherein $R_2$ and $R_3$ independently are hydrogen or $C_1$–$C_4$ alkyl and $Y_1$ is $OR_4$.

11. The method of claim 9 wherein (S)-benzyl 2-[2-(benzyloxy)phenyl]-2-thiazoline-4-carboxylate is administered.

12. The method of claim 9 wherein (S)-benzyl 2[2-benzyloxy)phenyl]-2-thiazoline-5-methyl-4-carboxylate is administered.

13. The method of claim 1 wherein X is O or S and Y is the fragment (1b).

14. The method of claim 13 wherein $R_3$ is and $Y_1$ is $OR_4$.

15. The method of claim 14 wherein benzyl 2-[2-(benzyloxy)phenyl]-2-oxazole-4-carboxylate is administered.

16. The method of claim 14 wherein 2-[2-(benzyloxy)phenyl]-2-oxazole-5-methyl-4-carboxylate is administered.

* * * * *